US008062722B2

(12) United States Patent
Blum et al.

(10) Patent No.: US 8,062,722 B2
(45) Date of Patent: Nov. 22, 2011

(54) CONDOM WITH WARMTH IMPARTING LUBRICANT

(75) Inventors: Dennis Blum, East Brunswick, NJ (US); James Daniels, Jr., Pennington, NJ (US); April Ensinger, Huntley, IL (US); Michael J. Harrison, Princeton, NJ (US); Robin Luyber, Delran, NJ (US); R. Christian Millar, Cream Ridge, NJ (US)

(73) Assignee: Church & Dwight Co., Inc., Princeton, NJ (US)

(*) Notice: Subject to any disclaimer, the term of this patent is extended or adjusted under 35 U.S.C. 154(b) by 330 days.

(21) Appl. No.: 10/598,366

(22) PCT Filed: Feb. 23, 2005

(86) PCT No.: PCT/US2005/005695
§ 371 (c)(1),
(2), (4) Date: Dec. 20, 2006

(87) PCT Pub. No.: WO2005/081952
PCT Pub. Date: Sep. 9, 2005

(65) Prior Publication Data
US 2008/0236595 A1 Oct. 2, 2008

(51) Int. Cl.
*A61F 6/04* (2006.01)
*B29D 22/00* (2006.01)
*B29D 23/00* (2006.01)
*B65D 85/08* (2006.01)

(52) U.S. Cl. ......... 428/35.2; 428/35.7; 128/844; 206/69

(58) Field of Classification Search ............... 428/35.2, 428/35.7; 128/842, 844, 918; 206/69
See application file for complete search history.

(56) References Cited

U.S. PATENT DOCUMENTS

| 4,840,188 | A | 6/1989 | Heidenfelder |
| 6,321,750 | B1 | 11/2001 | Kelly |
| 6,428,791 | B1 * | 8/2002 | Lezdey et al. ............ 424/195.17 |
| 6,536,438 | B1 | 3/2003 | Kakonyi |
| 7,005,408 | B2 | 2/2006 | Ahmad |
| 7,285,517 | B2 | 10/2007 | Ahmad |
| 7,417,013 | B2 | 8/2008 | Ahmad |
| 7,658,941 | B2 | 2/2010 | Ahmad |
| 7,695,730 | B2 | 4/2010 | Ahmad |
| 2002/0103414 | A1 * | 8/2002 | Harrison et al. ................. 600/29 |
| 2003/0211161 | A1 * | 11/2003 | Ahmad et al. ................. 424/488 |
| 2004/0167039 | A1 | 8/2004 | Ahmad |
| 2004/0185065 | A1 | 9/2004 | Ahmad |

OTHER PUBLICATIONS

Rowe R.C. et al. "Molecular weight dependence of the heats of hydration of some oligomeric ethylene oxides and their methoxyl derivatives" J. Applied Polymer Science, vol. 50, 321-326, 1993.
Rubino J.T. et al. "Cosolvency and deviations from log-linear solubilization" Pharmaceutical Research, vol. 4, No. 3, pp. 231-236, 1987.
Rytting E. et al. "A quantitative structure-property relationship for predicting drug solubility in PEG 400/water cosolvent systems" Pharmaceutical Research, vol. 21, No. 2, pp. 237-244, 2004.
Rubino J.T. et al. "Cosolvency and cosolvent polarity" Pharmaceutical Research, vol. 4, No. 3, pp. 220-230, 1987.
Avila C.M. et al. "Thermodynamic study of the solubility of benzocaine in some organic and aqueous solvents" Journal of Solution Chemistry, vol. 31, No. 12, pp. 975-985, 2002.

* cited by examiner

*Primary Examiner* — Rena Dye
*Assistant Examiner* — Erik Kashnikow
(74) *Attorney, Agent, or Firm* — Greenberg Traurig LLP; Jennifer A. Camacho

(57) ABSTRACT

A condom together with a lubrication composition, the lubricating composition containing a minimal amount of free water, and comprising one or more glycols, such that the glycols in the lubricant release heat and warmth when contacted with compositions containing free water.

9 Claims, No Drawings

CONDOM WITH WARMTH IMPARTING LUBRICANT

FIELD OF THE INVENTION

The field of the present invention relates generally to condoms, and more specifically to condoms having a lubricant system which imparts warmth, or provides a warming effect or sensation upon use.

BACKGROUND OF THE INVENTION

A variety of lubrication systems for condoms are disclosed in the art. Some of the lubricants employed are sold or supplied separately as so-called personal lubricants, while others are applied to condoms prior to packaging. Some lubricants have particular physiological effects. For example, Heidenfelder (U.S. Pat. No. 4,840,188) discloses the coating of the interior surface of a condom with a local anesthetic such as benzocaine to provide desensitization.

The instant invention is directed to a condom together with a lubricant which provides a warming effect or sensation upon use. This effect is in contrast to the cooling sensation imparted by conventional lubricants.

SUMMARY OF THE INVENTION

The present invention generally provides a condom in combination with a lubricant composition comprising one or more glycols. Such glycols, provided they are present in an environment relatively free from unbound water, will warm upon contact with compositions containing unbound water. Such warming of glycol based condom lubricants results in a warming sensation during condom use.

In one aspect of the present invention there is provided a condom comprising:

A male genital engaging tubular sheath having an inner surface and an outer surface together with a lubricant composition comprising one or more glycols in a mixture containing little or no unbound water, such that said lubricating composition warms upon contact with compositions containing free or unbound water.

DETAILED DESCRIPTION OF THE INVENTION

In one embodiment of the present invention, either the interior surface, the exterior surface, or both the interior and exterior surfaces are lubricated with a lubricant composition comprising one or more glycols in combination with a conventional lubricating gel. For example, propylene glycol and polyethylene glycol may be combined with a conventional lubricating gel such as the glyceryl polymethaylate based products sold by Guardian under the trademark Lubrajel CG. Optionally, glycerin (glycerol) may be added. This mixture will contain minimum amounts of water, as the Lubrajel CG has some water present. However, for example, the 24%-34% water found in Lubrajel CG is generally present in a bound form. Accordingly, the described lubricating composition contains relatively little free or unbound water. As a result, when this lubricating composition comes into contact with free water, as may be found in the bodily secretions which contact condoms during use, the glycerols react exothermically with the free water, resulting in an increase in lubricant temperature, and the imparting of a sense of warmth to the condom users. This is in contrast to conventional condom lubricating systems which typically impart a cooling sensation to the users.

Although conventional personal lubricants have in the past utilized glycols as an ingredient, free water generally has heretofore been utilized as a solvent. In such prior art compositions wherein free water has been present, as for example as a solvent, the presence of the free or unbound water in the glycol-containing lubricant compositions acts to minimize any noticeable heat of reaction upon contact of the lubricant with further water. Accordingly, the glycol containing lubricants found in the prior art imparted a cooling sensation to users. This is in marked contrast to the warming sensation imparted by the lubricating composition of the present invention, which contains glycols within a lubricant composition containing only minimal amounts of free water. There are examples in the art of lubricants which make use of the heat generated by the reaction of water and polyhydric alcohols. See US 2003/0211161 A1. Note, however, that application is not directed to the use of heating lubricants in connection with packaged condoms.

EXAMPLE 1

Preparation of a Lubricant Composition

A lubricant composition in accordance with the present invention having the formula shown in Table 1 was prepared as follows:

TABLE 1

| Ingredient | Percent w/w |
| --- | --- |
| Propylene Glycol | 20.0% w/w. |
| Polyethylene Glycol 400 | 45.0% w/w. |
| Lubrajel ® CG* | 25.0% w/w. |
| Glycerin 96% | 10.0% w/w. |
| | 100.0% |

*Lubrajel ® is a registered trademark of Guardian Chemical Corporation, Hauppauge, New York and contains glyceryl polymethacrylate, propylene glycol and water, the water being present in an amount of between about 24% to 34%, and said water being generally in a bound state, unable to undergo substantial reaction with the glycols present.

The lubricant described in Table 1 may be applied to a condom in a conventional fashion, wherein a portion of lubricant is shot into the interior of the condom and a portion of the lubricant is placed on the exterior. The so-coated condom may then be foil-wrapped using procedures common to the art. For coating purposes, it is preferred that 0.45 g to 0.75 g. of lubricant be applied to the exterior surface of the condom and 0.15 g to 0.45 g of the lubricant be applied to the interior surface. A typical method of applying lubricant to condom surfaces, such as is described in pending United States Patent Application 2002/0103414 A1 (which application is incorporated herein by reference), may be utilized in connection with the instant invention for application of the lubricant to the condom surfaces.

To demonstrate the temperature raising ability of the condom lubricant prepared in Example 1, a measurement was made of the temperature increase which took place when one (1) gram of the lubricant was mixed with one (1) gram of water. To measure this temperature increase, a sensitive thermocouple thermometer was affixed to the surface of a laboratory hotplate. The thermometer was set to record the temperature changes at a rate of one point per second for a 300 second (5 minute) time period. The hotplate was warmed to body temperature, approximately 98.6° F., to simulate in-use conditions. To further simulate in-use conditions, warm water, also approximately 98.6° F., was used to represent vaginal fluids. The thermometer recording was started, and after 15 seconds, 1 gram of the warm water was applied to the thermocouple.

A 4.0° F. drop in temperature followed the initial application of the warm water to the hotplate. Although both the hotplate and the water were at approximately the same temperature (98.6), the drop in temperature upon addition of water to the hot plate was related to the equipment set-up and the test being performed in the open-air, which permitted evaporative cooling to occur.

The water on the hotplate was then allowed to come into temperature equilibrium with the hotplate, and the temperature soon stabilized at about 94.0° F. At that point the lubricant (1 gram) was added to the water on the hotplate. The lubricant was at an ambient temperature (71° F.), which was chosen as being representative of lubricant temperature in a typical situation prior to use. This ambient temperature lubricant was mixed into the water. At that point there was a drop in temperature of 9.2° F. This drop was expected as the warm water had to equilibrate with the cooler lubricant. Over the next twenty (20) seconds, however, the lubricant/water mixture spontaneously heated to a temperature of 99.1° F., an increase of 14.3° F. from the lowest equilibrium temperature of the lubricant/water mixture, and 5.1° F. warmer than the temperature of the water before any lubricant was added.

This clearly demonstrated the heat producing property of the lubricant, which underwent an exothermic reaction, releasing a heat of solution as it dissolved in free water.

Although various embodiments of the invention have been shown and described, they are not intended to limit the invention as encompassed by the claims forming part of the application. Those of skill in the art may recognize certain modifications to these embodiments, which modifications are meant to be covered by the appended claims.

What is claimed is:

1. A packaged condom comprising: a male genital engaging tubular sheath having an inner surface and an outer surface together with a lubricating composition comprising glyceryl polymethacrylate and at least about 10% w/w propylene glycol and at least 30% w/w polyethylene glycol, wherein the amount of said polyethylene glycol is greater than the amount of said propylene glycol and minimal free water, wherein the lubricating composition is located on at least a portion of both the inner surface and the outer surface of the tubular sheath, wherein, when said condom is engaged on the genitalia of a male user, the lubricating composition warms upon contact with free water from bodily secretions of the user to provide a warming sensation to the user.

2. The condom of claim 1, wherein said lubricating composition further includes at least about 5% w/w glycerin.

3. The condom of claim 1, wherein the lubrication composition has the following formula: 20% w/w propylene glycol, 45% w/w polyethylene glycol, 25% w/w mixture of glyceryl polymethacrylate, propylene glycol and water, and 10% w/w glycerin 96%.

4. The condom of claim 3, produced by the process of applying from 0.45 g to 0.75 g of said lubricating composition to said outer surface, applying from 0.15 g to 0.45 g of said lubricating composition to said inner surface, then foil-wrapping said condom, wherein the amount of said lubricating composition applied to said outer surface is greater than the amount of said lubricating composition applied to said inner surface.

5. The condom of claim 1 wherein the lubricating composition contains no free water.

6. A packaged condom comprising:
a male genital engaging tubular sheath having an inner surface lubricated with a lubricating composition comprising glyceryl polymethacrylate and propylene glycol and at least about 30% w/w polyethylene glycol, wherein the amount of said polyethylene glycol is greater than the amount of said propylene glycol and minimal free water,
wherein, when said condom is in use and engaged on the genitalia of a male user, the lubricating composition mixes with free water from bodily secretions of the user in an exothermic reaction such that a warming sensation is provided to the user.

7. The packaged condom according to claim 6 wherein the lubricating composition comprises no free water.

8. The packaged condom according to claim 6, wherein the male genital engaging tubular sheath further comprises an outer surface lubricated with the lubricating composition.

9. The packaged condom according to claim 6, wherein the male genital engaging tubular sheath further comprises an outer surface lubricated with a second lubricating composition comprising one or more glycols and minimal free water such that the second lubricating composition will warm upon contact with free water.

\* \* \* \* \*

UNITED STATES PATENT AND TRADEMARK OFFICE
CERTIFICATE OF CORRECTION

| | | |
|---|---|---|
| PATENT NO. | : 8,062,722 B2 | Page 1 of 1 |
| APPLICATION NO. | : 10/598366 | |
| DATED | : November 22, 2011 | |
| INVENTOR(S) | : Blum et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Title page please insert reference to priority, below (65) Prior Publication Data, as follows:

--Related U.S. Application Data

(60) Provisional application No. 60/547,895, filed on February 26, 2004.--

Signed and Sealed this
Thirteenth Day of March, 2012

David J. Kappos
*Director of the United States Patent and Trademark Office*